(12) United States Patent
Itou et al.

(10) Patent No.: US 6,405,602 B1
(45) Date of Patent: Jun. 18, 2002

(54) MACHINE FOR INSPECTING CERAMIC SAMPLES BY APPLYING COMPRESSION THERETO

(75) Inventors: Nobuo Itou, Mie-gun; Shinichi Naruse; Mitsuo Takahashi, both of Nagoya, all of (JP)

(73) Assignee: NGK Insulators, Ltd. (JP)

( * ) Notice: Subject to any disclaimer, the term of this patent is extended or adjusted under 35 U.S.C. 154(b) by 0 days.

(21) Appl. No.: 09/610,939

(22) Filed: Jul. 6, 2000

(30) Foreign Application Priority Data

Jul. 28, 1999 (JP) .......................... 11-214061

(51) Int. Cl.[7] ................................ G01N 3/08
(52) U.S. Cl. ........................... 73/818; 73/790
(58) Field of Search ................... 73/807, 813, 818, 73/825, 826

(56) References Cited

U.S. PATENT DOCUMENTS 5,063,785 A * 11/1991 Labuz et al. ............... 73/821

FOREIGN PATENT DOCUMENTS

| JP | 45-8944 | 4/1970 |
|---|---|---|
| JP | 59-14048 | 1/1984 |
| JP | 60-129641 | 7/1985 |
| JP | 6-69815 | 9/1994 |
| JP | 10-197429 | 7/1998 |

* cited by examiner

Primary Examiner—Benjamin R. Fuller
Assistant Examiner—Andre Allen
(74) Attorney, Agent, or Firm—Parkhurst & Wendel, LLP

(57) ABSTRACT

A machine for inspecting a ceramic sample by applying a compression thereto, includes an inspecting container including a generally cylindrical container provided with an elastic sleeve therein. An elastic sheet is disposed between the cylindrical container and the elastic sleeve. The cylindrical container and the elastic sleeve and sheet are integrated to form the inspecting container. A ceramic sample provided in the cylindrical container is compressed by injecting a hydrostatic pressure applying medium between the elastic sheet and the cylindrical container.

4 Claims, 5 Drawing Sheets

7kg

15kg

MAXIMUM LOAD 5kg

10kg

MACHINE FOR INSPECTING CERAMIC SAMPLES BY APPLYING COMPRESSION THERETO

BACKGROUND OF THE INVENTION

1. Field of the Invention

The present invention relates to an inspection machine by compression for ceramic samples, and in particular, for ceramic samples having honeycomb structures.

2. Description of Related Art

Inspections by compression on a ceramic structure, such as a honeycomb structure, is performed by applying hydrostatic pressure on the ceramic structure. FIG. 4 is a perspective view of a conventional inspection method by compression having a configuration in which a sample 1, disposed in a urethane rubber cylinder 2 having an internal diameter corresponding to the diameter of the sample 1 and having a thickness of 1 to 2 mm, is provided with disk-like acrylic plates 3 attached to the sample 1 at the ends thereof, the acrylic plates 3 are fixed to the urethane rubber cylinder 2 by elastic bands 4, and the sample 1 covered by the urethane rubber cylinder 2 and the acrylic plates 3 is placed in water in a tank 5, whereby pressure is applied to the sample 1.

However, a problem in the above-described conventional inspection method by compression has been found to be that the efficiency of operation decreases when many samples are inspected because it is time-consuming to fix the acrylic plates 3 to the urethane rubber cylinders 2 by the elastic bands 4. Another problem is that it is difficult to clean the inspection device after inspecting when wet fractions of samples, which have been broken by the pressure, adhere to the urethane rubber cylinders.

In order to overcome these problems, an inspection machine by compression is disclosed in, for example, Japanese Unexamined Patent Application Publication No. 10-197429, in which the inspection machine is provided with a cylindrical container, a urethane sleeve, and a urethane sheet. Inspecting using this inspection machine by compression is performed as follows. Referring to FIG. 5, a sample 1 provided with a urethane sleeve 7 around the same is placed in a cylindrical container 8 with a urethane sheet 9 disposed between the urethane sleeve 7 and the cylindrical container 8. A hydrostatic-pressure-applying medium is injected between the cylindrical container 8 and the urethane sheet 9, thereby compressing the sample 1 at the periphery thereof, whereby the inspection by compression is performed.

In this inspection machine by compression, the sample 1 is not fixed by elastic bands. Therefore, the efficiency of operation is not decreased when many samples are processed. Moreover, after inspecting, dry fractions of the sample 1 remain in the urethane sleeve 7. Therefore, cleaning of the inspection machine is easier than when using the urethane rubber cylinder 2 shown in FIG. 4.

However, a problem in the inspection machine by compression 1 shown in FIG. 5 is that it is difficult to control the pressure applied to the sample 1, because the compression of the sample 1 does not properly respond to the pressure applied to the pressure-applying medium due to the elasticity of the urethane sleeve 7.

Another problem is that it is difficult to apply a low pressure of not greater than 10 kg/cm$^2$ to the sample 1 due to the elasticity of the urethane sleeve 7. That is, when the pressure on the sample 1 is desired to be at a pressure of 10 kg/cm$^2$ or less, the pressure applied to the pressure-applying medium serves only to compress the urethane sleeve 7 and does not compress the sample 1.

Yet another problem has been found in the inspection machine by compression 1 shown in FIG. 5, in that a tact time of the test must be set to be long when a high pressure is applied to the sample 1, because there is a time lag before a pressure-load reaches the sample 1 after the pressure is applied to the inspection machine, the time lag being caused by the elasticity of the urethane sleeve 7, thereby reducing the efficiency in the operation. Furthermore, when a high pressure-load is applied in a short time, there is a risk of breaking the sample 1 by the shock of the pressure. Generally, when a lot of samples are inspected at high pressures, tact time required per sample for the inspection must be reduced so as to increase the efficiency of the inspection.

In the inspection machine by compression 1 shown in FIG. 5, the preparations for the inspection are laborious, in which each sample must be inserted to the urethane sleeve 7, then must be disposed in the cylindrical container 8. An easy method for cleaning the fractions of the sample 1 is also necessary.

SUMMARY OF THE INVENTION

Accordingly, it is an object of the present invention to provide an inspection machine by compression in which inspection operation and cleaning of the inspection machine are easy, application of a low pressure is possible, and a tact time required per sample for the inspection is reduced, thereby increasing the efficiency of the inspection.

To these ends, an inspection machine by compression for inspecting a ceramic sample is provided, in which the ceramic sample covered by an elastic sleeve disposed at the periphery of the sample is received in a cylindrical container across an elastic sheet provided between the cylindrical container and the elastic sleeve, and the ceramic sample is compressed by a hydrostatic-pressure-applying medium injected between the cylindrical container and the elastic sheet. The sample is received in an inspecting container provided with the cylindrical container including the elastic sleeve and the elastic sheet between the elastic sleeve and an inner wall of the cylindrical container.

In the inspection machine by compression according to the invention, the elastic sleeve is preferably brought into contact with the sample by high-speed-pressurizing, and may be compressed so as to apply pressure to the sample by low-speed-pressurizing. In the inspection machine by compression, the beginning of fracture of the sample is preferably determined by detecting fracture sound from the sample, thereby suspending pressurization.

In the inspection machine by compression according to the invention, the sample may have a honeycomb structure. The elastic sheet and the elastic sleeve may be made of urethane.

DESCRIPTION OF THE PREFERRED EMBODIMENTS

Figure 1:
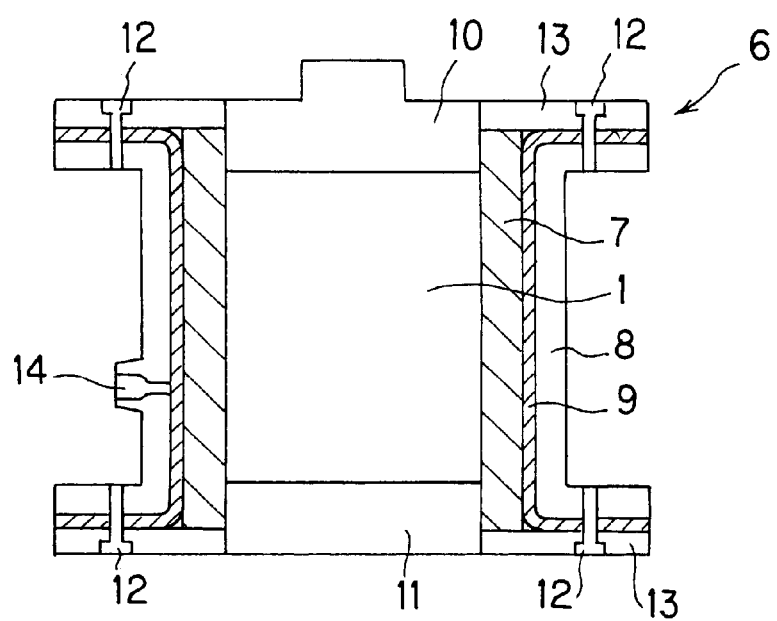
FIG. 1 is a schematic section of an inspection machine by compression according to an embodiment of the present invention.
Figure 5:
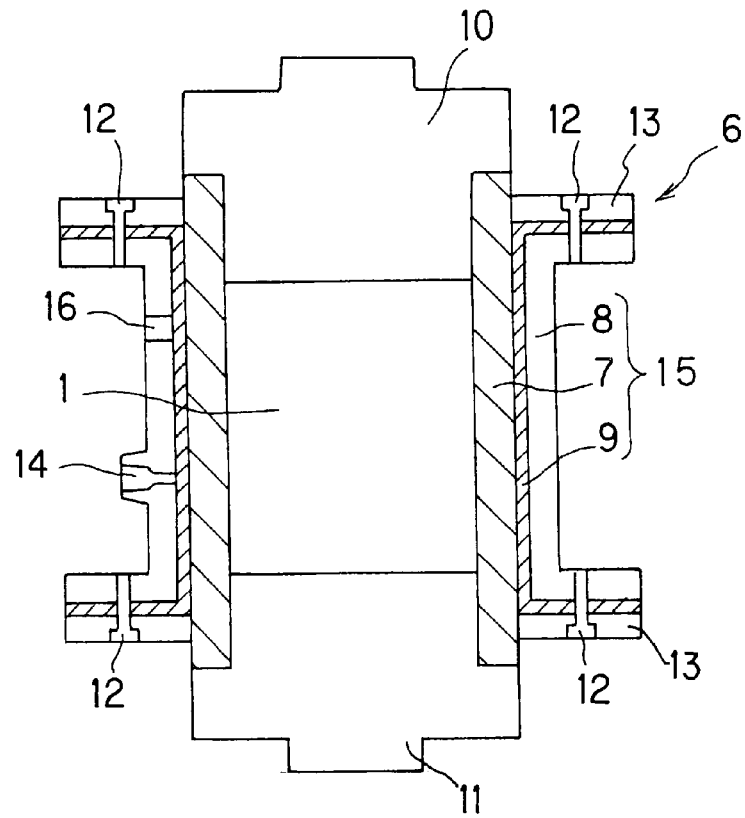
FIG. 5 is a schematic section of another known inspection machine by compression.

In an inspection machine by compression according to an embodiment of the present invention, a ceramic sample provided with an elastic sleeve around the same is disposed in a cylindrical container across an elastic sheet between the elastic sleeve and the cylindrical container, and a hydrostatic-pressure-applying medium is injected between the cylindrical container and the elastic sheet and is pressurized, whereby an inspection by compression is performed on the ceramic sample. As shown in FIG. 1, a sample 1 is received in an inspecting container 15 including a cylindrical container 8, an elastic sleeve 7, and an elastic sheet 9 disposed between the cylindrical container 8 and the elastic sleeve 7. Since the cylindrical container 8, the elastic sheet 9, and the elastic sleeve 7 are assembled to form an inspecting container 15, it is not necessary to insert each sample 1 to the urethane sleeve 7, and to insert the urethane sleeve 7 containing the sample 1 to the cylindrical container 8. Therefore, this is prepared in a manner simpler than in a conventional inspecting machine by compression shown in FIG. 5. In the inspecting machine by compression according to the embodiment of the invention, the pressure rise is suspended by detecting a fracture sound from the inspecting sample; therefore, the sample is not broken further than is necessary, whereby fractions of the sample can be easily cleaned compared with the conventional inspection machine by compression shown in FIG. 5.

In the inspection machine by compression according to the present invention, the elastic sleeve 7 is preferably pressed to the sample 1 at a high-speed pressurizing of 2 to 6 kg/cm$^2$/second, and is preferably pressed so as to compress the sample 1 at a low-speed pressurizing of 0.5 to 1 kg/cm$^2$/second, wherein "high-speed pressurizing" and "low-speed pressurizing" means respective high and low rates of change in pressure. By applying pressure in steps at different pressurizing speeds, an efficient inspection in a short tact time is possible when applying a high pressure. The high pressurizing speed is possible due to the fact that there is no risk of fracturing the sample 1 by the shock at high pressurizing speed, because the sample 1 is not pressed by the elastic sleeve 7 for a time after the pressurizing starts until the elastic sleeve 7 presses the sample 1, the time lag being produced by the elasticity of the elastic sleeve 7. With this arrangement, a tact time per sample is conveniently reduced. When the elastic sleeve 7 is compressed to press the sample 1, a load starts to be applied to the sample 1; therefore, the pressure must be applied at a low speed so as to avoid fracturing the sample 1 due to shocks.

With this arrangement in which the pressure is applied in steps, time saving by pressing the elastic sleeve 7 to the sample 1 at a high speed can be realized together with low-speed pressurizing which is required for applying a low pressure-load to the sample 1. A maximum pressure is obtained by the low-speed pressurizing, thereby improving response of the pressure applied to the sample 1 to the pressure applied to the elastic sleeve 7. The timing of switching from the high-speed pressurizing to the low-speed pressurizing is determined by detecting the mechanical position of a cylinder head for producing compression to apply hydrostatic pressure between the cylindrical container 8 and the elastic sheet 9, or by detecting the hydrostatic pressure value. FIGS. 3A to 3D are graphs showing pressure curves in accordance with the elapse of time when the maximum load value is set to 5 kg, 7 kg, 10 kg, and 15 kg, respectively. In each graph, a solid line represents values of pressure applied to the sample and measured by a load cell, and dotted lines represent values of hydrostatic pressure detected by a pressure sensor.

The inspection machine by compression according to the present invention preferably determines the start of fracture of the sample by detecting a fracture sound from the sample, thereby suspending pressurizing. The sample is prevented from being unnecessarily broken by suspending pressurizing when the start of fracture of the sample is detected either by detecting a fracture sound at the beginning of fracture of the ceramic sample by an acoustic emission (AE) sensor, or by detecting the change in hydrostatic pressure due to the fracture of the sample, whereby excessive fracturing of the sample does not occur, thereby making cleaning easier.

Figure 2A:
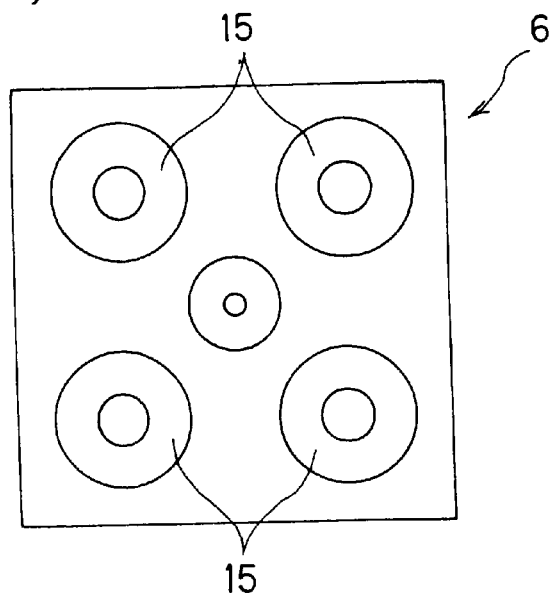
FIG. 2A is a schematic plan view of an inspection machine by compression according to another embodiment of the present invention.
Figure 2B:
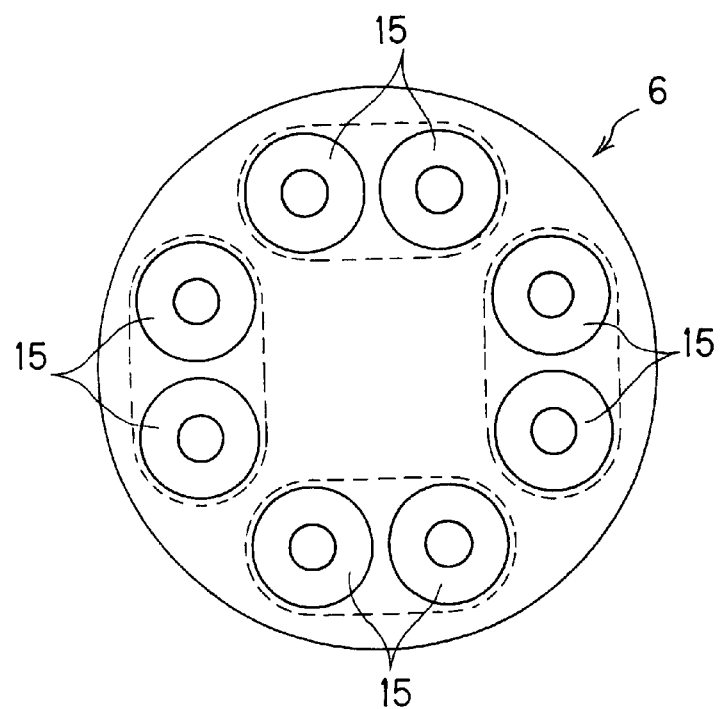
FIG. 2B is a schematic plan view of an inspection machine by compression according to yet another embodiment of the present invention.
Figure 3B:
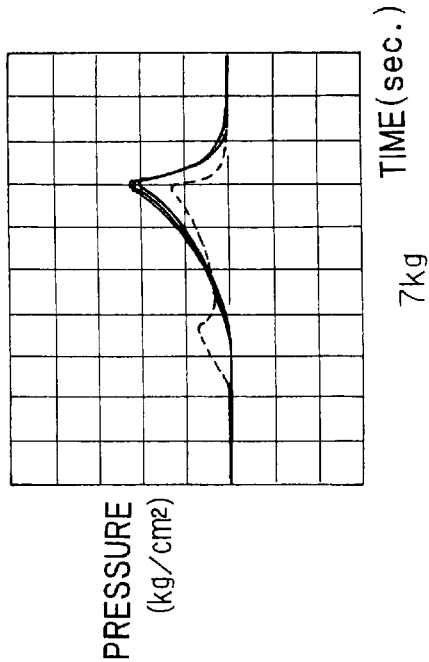
FIGS. 3A, 3B, 3C, and 3D are graphs showing pressure curves when inspecting by using the inspection machine by compression according to the present invention, in which the maximum load values are set to 5 kg, 7 kg, 10 kg, and 15 kg, respectively.
Figure 3D:
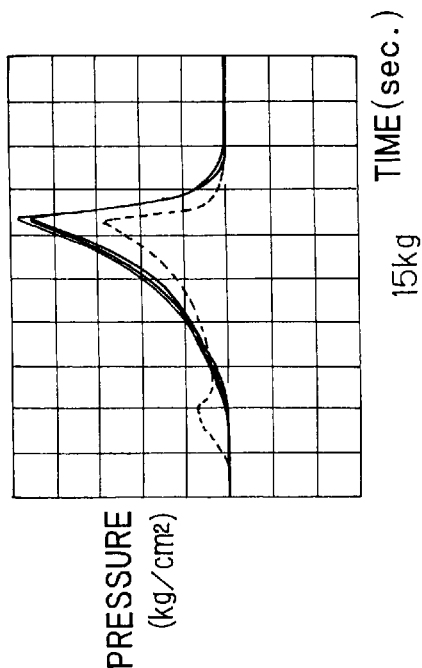
Figure 3A:
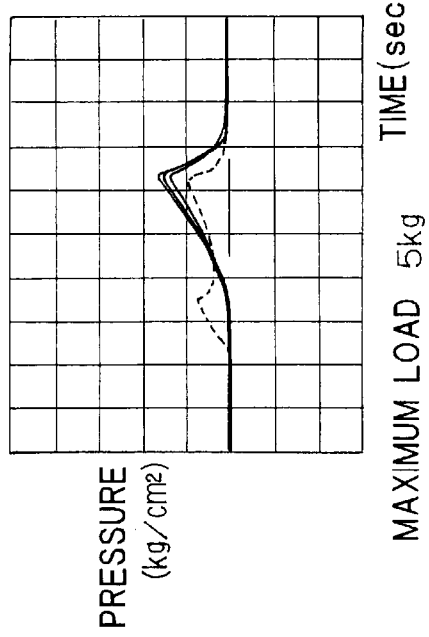
Figure 3C:
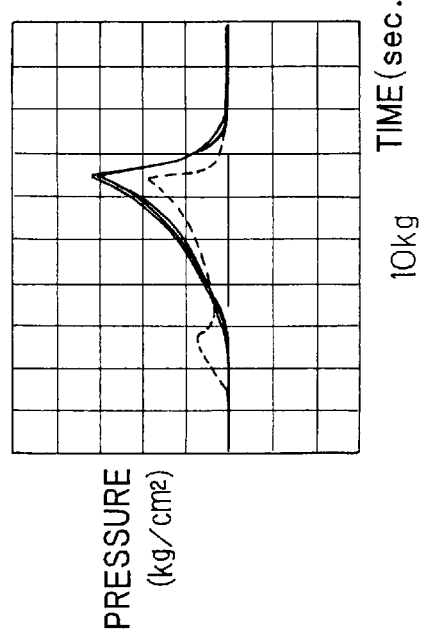
Figure 4:
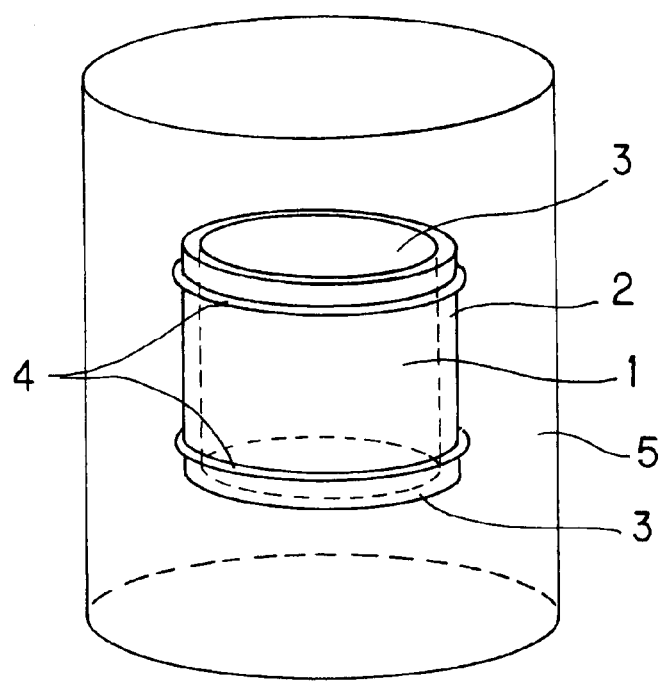
FIG. 4 is a perspective view of a known inspection machine by compression.

FIG. 2A. is a plan view of an inspection machine by compression 6 according to another embodiment of the present invention, in which four inspecting containers 15 are provided, samples are loaded and unloaded to and from the inspection machine by compression 6 at one position, the pressure is applied at one position, and an operator, without changing his/her position, can perform the inspection by compression successively by turning the four inspecting containers. FIG. 2B is a plan view of an inspection machine by compression 6 according to yet another embodiment of the present invention, in which eight inspecting containers 15 are provided in four pairs, and samples are loaded into and unloaded from the inspection machine by compression 6, and the pressure is applied at one position. Two samples received in a pair of the inspecting containers 15 are inspected concurrently, thereby making the inspection efficient.

The inspection machine by compression according to the present invention is preferably used for an inspection by compression for ceramic samples, in particular, for an inspection by compression of ceramic honeycomb structures.

The present invention is described below with reference to an experimental operation performed by using an example of the inspection machine by compression according to the invention. It is to be understood that the invention is not limited to this example.

Figure 6:
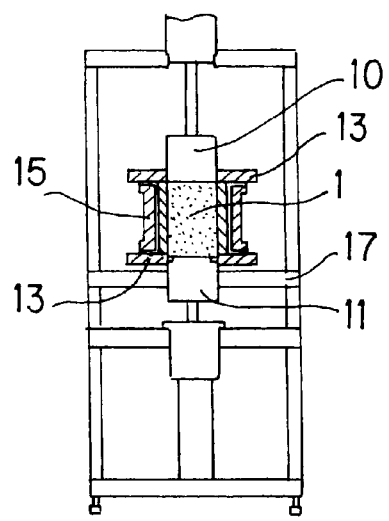
FIG. 6 is a schematic section of the inspection machine by compression according to the present invention, by the use of which an inspection is performed.

Referring to FIGS. 1 and 6, an inspection by compression of a ceramic honeycomb structure was performed by using an inspection machine by compression 6 including an inspecting container 15 having a cylindrical container 8, a urethane sheet 9, and a urethane sleeve 7.

The cylindrical container 8 made of iron is provided with the urethane sheet 9 having a thickness of 2 to 5 mm at an inner side of the cylindrical container 8. The urethane sheet 9 is hermetically fixed to the cylindrical container 8 by being clamped at each side of the urethane sheet 9 by an annular edge and a flange 13 formed at each end of the cylindrical container 8 and by screws 12 passing through the annular edge and the flange 13. The urethane sleeve 7 having a thickness of 10 to 30 mm is disposed at the inner side of the urethane sheet 9. The urethane sleeve 7 is fixed to the cylindrical container 8 by coupling therewith. The cylindrical container 8 is provided with an air outlet 14 and a pressure inlet 16 connectable with a pressure hose of a compressing unit (not shown).

During inspecting, the inspecting container 15 was fixed to a base 17, as shown in FIG. 6. A supporting cylinder 11 was moved to the upper level of the cylindrical container 8, a honeycomb structure 1 was mounted on the supporting cylinder 11, the supporting cylinder 11 was moved down to the lower level of the inspecting container 15, and the honeycomb structure 1 was thus received in the inspecting container 15. A retaining cylinder 10 was disposed on the honeycomb structure 1, and the supporting cylinder 11 and the retaining cylinder 10 clamped the honeycomb structure 1 with a force of approximately 10 kgf/cm$^2$ so that the honeycomb structure 1 did not move with the pressure applied thereto.

Water was injected between the cylindrical container 8 and the urethane sheet 9 through an injecting valve (not shown) being released. While injecting water, the air between the cylindrical container 8 and the urethane sheet 9 was released through the air outlet 12, and the air outlet 12 was closed after the water was injected. Then, the compressing unit (not shown) started to apply pressure through the pressure hose. The pressure was applied for a second by a high-speed pressurizing of 5 kg/cm$^2$/second to a level of 5 kg/cm$^2$, thereby pressing the urethane sleeve 7 to the honeycomb structure 1 and compressing the urethane sleeve 7.

Next, the honeycomb structure 1 started to be compressed by a low-speed pressurizing of 1 kg/cm$^2$/second. The timing of switching from the high-speed pressurizing to the low-speed pressurizing was determined by detecting the mechanical position of a cylinder head for producing compression for applying hydrostatic pressure between the cylindrical container 8 and the elastic urethane sheet 9. When the pressure was applied, the urethane sleeve 7 came into contact with the periphery of the honeycomb structure 1, thereby evenly pressing the entire periphery thereof. FIG. 6 shows the inspection machine by compression 6 while performing the inspection. In the inspection, the honeycomb structure 1 cracked when the pressure rose to 5 kg/cm$^2$ in one second; therefore, the pressurizing was suspended, and the pressure was reduced. The cracking was detected by an AE sensor (not shown) provided on the retaining cylinder 10.

By using the above-described inspection machine by compression according to the present invention, an inspection by compression can be easily performed compared with the case in which a conventional inspection machine by compression is used, thereby increasing the efficiency of the test. In the inspection machine by compression, a sample is not broken more than necessary because pressure-rise is suspended by detecting a fracture sound from the sample, whereby fractions of the sample can be cleaned up easily.

In the inspection machine by compression according to the present invention, when the pressure is applied in steps, a test under a low pressure is possible, and an efficient inspection in a short tact time is also possible when a high pressure is applied. The response in the pressure rise on the sample to the pressure applied to a pressure-applying medium can be improved, thereby facilitating control of the pressure applied to the sample.

In the inspection machine by compression according to the present invention, the beginning of breakage of a sample is detected by sensing fracture sound from the sample, and the pressure-rise is suspended, thereby avoiding unnecessary breakage of the sample, whereby fractions of the sample can be cleaned up more easily.

What is claimed is:

1. A machine for inspecting a ceramic sample by applying a compression force thereto, comprising:

an inspecting container including a generally cylindrical container provided with an elastic sleeve therein;

an elastic sheet disposed between said cylindrical container and said elastic sleeve; and means for compressing a ceramic sample in said cylindrical container by injecting a hydrostatic pressure applying medium between said elastic sheet and said cylindrical container at a high rate of change in pressure and at a low rate of change in pressure, wherein said elastic sleeve is capable of and positioned for contacting such a sample at said high rate of change in pressure and then compressing such a sample at said low rate of change in pressure, and said cylindrical container, said elastic sheet and said elastic sleeve are integrated to form said inspecting container.

2. The machine of claim 1, further comprising means for determining the beginning of sample fracture by detecting a sound from the sample and suspending compression thereof.

3. The machine of claim 1, wherein the sample comprises a honeycomb structure.

4. The machine of claim 1, wherein said elastic sheet a said elastic sleeve are each made of urethane.

* * * * *